(12) United States Patent
Oehlinger

(10) Patent No.: US 7,626,022 B2
(45) Date of Patent: Dec. 1, 2009

(54) METHOD FOR PRODUCING β-HETEROARYL-α-ALANINE COMPOUNDS USING 2-AMINO-2-(HETEROARYLMETHYL) CARBOXYLIC ACID COMPOUNDS

(75) Inventor: Stefan Oehlinger, Berlin (DE)

(73) Assignee: chiracon GmbH, Luckenwalde (DE)

( * ) Notice: Subject to any disclaimer, the term of this patent is extended or adjusted under 35 U.S.C. 154(b) by 499 days.

(21) Appl. No.: 10/889,355

(22) Filed: Jul. 12, 2004

(65) Prior Publication Data

US 2005/0080263 A1 Apr. 14, 2005

(30) Foreign Application Priority Data

Jul. 11, 2003 (DE) ................ 103 32 560

(51) Int. Cl.
*C07D 241/42* (2006.01)
*C07F 7/02* (2006.01)
*C07D 241/06* (2006.01)

(52) U.S. Cl. .............. 544/353; 544/350; 544/229; 544/336; 514/249; 514/250; 514/252.1

(58) Field of Classification Search ............ 544/350, 544/353, 336, 229
See application file for complete search history.

(56) References Cited

U.S. PATENT DOCUMENTS 6,451,821 B1 * 9/2002 Carry et al. ............ 514/342

OTHER PUBLICATIONS

Haggerty et al, "Amino Acids. I. DL-β-(Diazaphenyl)alanaines (I)" Journal of Heterocyclic Chemistry, vol. 2(1), pp. 1-6 (Mar. 1965).*
Patchornic and Shaltiel, "Nonenzymic Cleavage of HIstidyl Peptide Bonds" Peptides, Proc. European Symp., 6$^{th}$, Athens, pp. 177-182 (1966), As Abstracted by Caplus.*
Petermann and Fauchere, "Synthesis of β-Pyrazinyl-L-Alanine (Paa) and of Peptide Derivatives" Helvetica Chimica Acta, vol. 66(5), pp. 1513-1518 (1983), As Abstracted by Caplus.*
Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Dale L. Boger et al.; DNA Binding Properties of Key Sandramycin Analogues: Systematic Examination of the Intercalation Chromophore; *Bioorganic & Medicinal Chemistry* 7, 1999, pp. 315-321.
Margaret M. Harding et al.; DNA-Binding Studies of XSPTSPSZ, Derivatives of the Intercalating Heptad Repeat of RNA Polymerase II; *Biopolymers* 42, 1997, pp. 387-398.
Walter Ried and H. Schiller; Über heterocyclisch substituierte Aminosäuren, I. Mitteil.: Die Synthese einiger heterocyclisch substituierter α-Amino-säuren und α-Imino-säureester; *Chem. Ber.* 86. 1953, pp. 730-734.
Walter Ried and Willi Reitz; Über heterocyclisch substituierte Aminosäuren. III. Mitteil.: Kondensation heterocyclischer Brenztraubensäureester mit Hippursäure: *Chem. Ber.* 89, 1956, pp. 2429-2433.
Guy Y. Krippner and Margaret M. Harding; Intercalator Amino Acids: Synthesis of Heteroaryl Alanines; *Tetrahedron: Asymmetry* vol. 5, No. 9, 1994. pp. 1793-1804.
Xiaofen Huang and Eric C. Long, Chemoenzymatic Synthesis and Incorporation of L-2-Quinoxalytalanine into a Tandem β-Turn Peptide Motif; *Bioorganic & Medicinal Chemistry Letters* vol. 5, No. 17, 1995, pp. 1937-1940.
Gaston L. Schmir and Louis A. Cohen; Oxidative Degradation of Imidazoles by Bromine or N-Bromosuccinimide; *Biochem.* vol. 4, No. 3, Mar. 1965, pp. 533-538.
Robert M. Adlington, et al.; A versatile synthetic route to quinoxaline, pyrazine and 1,2,4-triazine substituted α-amino acids from vicinal tricarbonyls; *J. Chem. Soc., Perkin Trans.* 1, 2000, pp. 299-302.
Robert M. Adlington, et al.; The efficient enantioselective synthesis of quinoxaline, pyrazine and 1,2,4-triazine substituted α-amino acids from vicinal tricarbonyls; *J. Chem. Soc., Perlin Trans.* 1, 2001, pp. 668-679.
Paul Darkins, et al.; Enantiopure N-protected α-amino glyoxals 1. Synthesis from α-amino acids and some condensation reactions with amines; *J. Chem. Soc., Perkin Trans.* 1, 2000, pp. 381-389.
Chi-Nung Hsiao, et al.; Synthesis of N-(Tert-Butoxycarbonyl)-3-(4-Thiazolyl)-L-Alanine; *Synthetic Communications*, 20(22), 1990, pp. 3507-3517.
John R. Johnson and W.L. McEwen; 1,2,3-Tribromopropane, $CH_2BrCH=CH_2+Br_2 \rightarrow CH_2BrCHB,CH_2Br$; *Org. Synth. Coll*, vol. 1, 1932, pp. 521-522.
R. Lespieau and M. Bourguel; 2,3-Dibromopropene, (Propene, 2,3-dibromo-) $CH_2BrCHBrCH_2Br+NaOH\wedge CH_2BrCB_{re}CH_2+NaBr+H_2O$; *Org. Synth. Coll.*, vol. 1, 1932, pp. 209-211.
M. Robert Leanna and Howard E. Morton; N-(Boc)-L-(2-Bromoally)-Glycine: A Versatile Intermediate for the Synthesis of Optically Active Unnatural Amino Adds; *Tetrahedron Letters*, vol. 34, No. 26, 1993, pp. 4485-4488.

* cited by examiner

*Primary Examiner*—Brenda L Coleman
*Assistant Examiner*—Susanna Moore
(74) *Attorney, Agent, or Firm*—The Webb Law Firm

(57) ABSTRACT

This invention relates to N and O-protected, optionally substituted β-heteroaryl-α-alanine compounds of the structural Formula I,

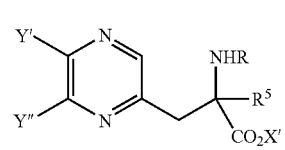

wherein each of the variables is as set forth in the specification, methods for producing and using the same.

6 Claims, No Drawings

METHOD FOR PRODUCING β-HETEROARYL-α-ALANINE COMPOUNDS USING 2-AMINO-2-(HETEROARYLMETHYL) CARBOXYLIC ACID COMPOUNDS

BACKGROUND OF THE INVENTION

1. Field of the Invention

This invention relates to N-protected, optionally substituted β-heteroaryl-α-alanine compounds (also referred to herein as 2-amino-3-(heteroaryl)-propionic acid compounds), and N- and O-protected, optionally substituted 2-amino-2-(heteroarylmethyl)-carboxylic acid compounds, particularly propionic acid and malonic acid compounds, methods of their production, and the use of N- and O-protected, optionally substituted 2-amino-2-(heteroarylmethyl)-carboxylic acid compounds for producing N-protected, optionally substituted β-heteroaryl-α-alanine compounds.

2. Description of the Related Art

Some natural peptides such as sandramycin, luzopeptin, quinaldopeptin, and quinoxapeptin show high biological activity. These depsipeptides are known as quinomycins and triostins. They have antibiotic, antiviral, and/or antitumoral effects (D. L. Boger et al.: *Bioorg. Med. Chem.* 7, 1999, 315-321). Synthetic peptides, particularly those including β-heteroaryl-α-amino acids, show bioactivity as well (M. M. Harding et al.: *Biopolymers* 42, 1997, 387-398).

Various methods are known to produce β-heteroaryl-α-amino acids such as β-(2-quinoxalinyl)-α-alanine.

Attempts at producing β-(2-quinoxalinyl)-α-alanine by reduction of the oxime of quinoxalic pyruvic acid with hydrogen (W. Ried, H. Schiller: *Chem. Ber.* 86, 1953, 730-734) or by reductive splitting of azlactone from quinoxalic pyruvic acid with glacial acetic acid, hydriotic acid and red phosphor (W. Ried, W. Reitz: *Chem. Ber.* 89, 1956, 2429-2433) yielded the corresponding diketopiperazine under dimerization. Acidic hydrolytic cleavage of diketopiperazine yielded a small quantity of β-(2-quinoxalinyl)-α-alanine.

Reaction of 2-quinoxalinmethyl halogenides with N-tert.-butyloxycarbonyl imidazolidinone (G. Y. Kripper, M. M. Harding: *Tetrahedron: Asymmetry* 5, 1994, 1793-1804) or reaction with N-(diphenylmethylene)-glycinmethyl ester (X. Huang, E. C. Long: *Bioorg. Med. Chem. Lett.* 5, 1995, 1937-1940) in the presence of a base and subsequent hydrolysis of the condensates resulted in β-(2-quinoxalinyl)-α-alanine. The 2-quinoxalinmethyl halogenides used are unstable and can only be produced at low quantities in a sophisticated synthesis procedure. Imidazolidinone is commercially available at high prices.

β-(2-quinoxalinyl)-α-alanine compounds were produced by reacting 4,5-dioxo-2-aminopentanoic acid compounds with 1,2-phenylenediamine (G. L. Schmir, L. A. Cohen: *Biochem.* 4, 1965, pp. 533-538; J. E. Baldwin et al.: *J. Chem. Soc., Chem. Commun.* 2000, pp. 299-302; J. E. Baldwin et al.: *J. Chem. Soc., Perkin Trans.* 1, 2001, pp. 668-679; M. Nieuwnhuyzen et al.: *J. Chem. Soc., Perkin Trans.* 1, 2000, pp. 381-389). For example, N-benzoyl-protected 4,5-dioxo-2-amino-pentanoic acid was obtained in situ by reacting N-benzoyl histidine with N-bromosuccinimide. The more recent (Baldwin et al.; Nieuwnhuyzen et al.: loc. cit.) syntheses mentioned here have the disadvantage that they need larger quantities of dimethyl dioxirane, a scarcely available oxidant.

The known methods of producing β-(2-quinoxalinyl)-α-alanine compounds thus all have disadvantages. They require synthesis of hardly accessible precursors, involve unstable intermediates, have a small yield only and require extensive purification.

It is the problem of this invention to provide novel compounds for synthesizing bioactive peptides and methods for their production. These methods should start from easily accessible, inexpensive parent compounds, involve stable intermediates, allow simple and fast execution, produce high yields, and involve simple purification methods. In addition, they should facilitate the yield of enantiomerically pure compounds.

SUMMARY OF THE INVENTION

This problem is solved according to the invention by providing N and O-protected or N or O-protected, optionally substituted β-heteroaryl-α-alanine compounds from N and O-protected or N or O-protected, optionally substituted 2-amino-2-(heteroarylmethyl) carboxylic acid compounds and by providing methods for producing the respective 2-amino-2-(heteroarylmethyl) carboxylic acid compounds. The invention is particularly suited for providing enantiomerically pure N and O-protected or N- or O-protected, optionally substituted β-heteroaryl-α-alanine compounds from enantiomerically pure 2-amino-3-(heteroarylmethyl)-carboxylic acid compounds according to the invention.

DETAILED DESCRIPTION OF THE INVENTION

The object of the invention are β-heteroaryl-α-alanine compounds, optionally substituted, of the general formula I,

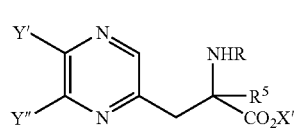

I wherein $R^5$ is a hydrogen atom or a $CO_2X''$ group in which X'' represents an alkyl, aryl, or amino group $-NR^6R^7$ in which $R^6$ and $R^7$ are same or different and represent a hydrogen, alkyl, or aryl residue, and wherein X'' preferably has the same meaning as X', R represents an alkyloxycarbonyl residue such as
tert.-Butoxycarbonyl-(Boc-),
9-Fluorenylmethoxycarbonyl (Fmoc-),
Methyloxycarbonyl,
Ethyloxycarbonyl,
Allyloxycarbonyl (Alloc-),
Benzyloxycarbonyl (Cbz or Z protective group),
9-(2,7-Dibromo)-fluorenylmethyloxycarbonyl,
9-[2,7-Bis(trimethylsilyl)]-fluorenylmethyloxycarbonyl-(2,7-Bts-Fmoc-),
9-(2,6-Di-tert-butyl)-fluorenylmethyloxycarbonyl-(2,6-Dtb-Fmoc- or Fmoc*-),
9-(2,7-Di-tert-butyl)-fluorenylmethyloxycarbonyl-(2,7-Dtb-Fmoc-),
2,2,2-Trichloroethyloxycarbonyl (Troc-),
2-Trimethylsilylethyloxycarbonyl (Teoc-),
p-Methoxybenzyloxycarbonyl (Moz-),
p-Nitrobenzyloxycarbonyl (PNZ-),
4-Methylsu Ifinylbenzyloxycarbonyl (Msz-),
6-Nitroveratryloxycarbonyl groups (Nvoc-)

or

R represents an acyl group such as

Acetyl, trifluoroacetyl, propionyl, pivaloyl, 4-pentenoyl, 2,2-dimethyl-4-pentenoyl, benzoyl, phthalyl groups, X' represents a hydrogen atom, an alkyl or aryl group that may be substituted such as Methyl, ethyl, propyl, butyl, benzyl, aryl-substituted benzyl, trimethylsilylethyl, tert.-butyl, neopentyl, 2,2,2-trichloroethyl groups, or an amino group —$NR^6R^7$ wherein $R^6$ and $R^7$ are same or different and represent a hydrogen atom, an alkyl or aryl residue, Y' and Y" represent hydrogen or together form a

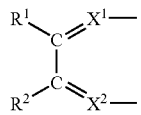

chain wherein $X^1$ is nitrogen or a $CR^3$ group, $X^2$ is nitrogen or a $CR^4$ group, $R^1$ and $R^2$ are same or different and each represent a hydrogen atom, a halogen atom, a substituent alkyl residue, an alkyl group with one or more additional fluorine atoms, an alkoxy group, or together form an—optionally substituted—aromatic ring system, $R^3$ and $R^4$ are same or different and each represent a hydrogen atom, a halogen atom, an alkyl group with one or more additional fluorine atoms, and/or an alkoxy group, in the form of their diastereomers, enantiomers, and mixtures thereof including their racemates—boc-protected compounds exclusively in the form of their racemates—and in the form of free bases, salts and/or solvates as well as their solutions, which may be crystalline, particularly for fmoc compounds.

Particularly preferred are compounds selected from the group of 2-acetamido-3-(2-quinoxalinyl) propionic acid ethyl ester, N-boc-β-(2-quinoxalinyl)-α-alanine, N-fmoc-β-(2-quinoxalinyl )-α-alanine, N-acetyl-β-(2-quinoxalinyl )-α-alanine.

N-phthalimido-β(2-quinoxalinyl)-α-alanine,

N-(pent-4-enoyl)-β-(2-quinoxalinyl)-α-alanine, 2-acetamido-2-(2-quinoxalinylmethyl) malonic acid diethyl ester, 2-benzamido-2-(2-quinoxalinylmethyl) malonic acid diethyl ester, 2-phthalylimino-2-(2-quinoxalinylmethyl) malonic acid diethyl ester, 2-benzamido-2-(2-quinoxalinylmethyl) malonic acid diethyl ester, 2-phthalylimino-2-(2-quinoxalinylmethyl) malonic acid diethyl ester, 2-acetamido-2-(2-quinoxalinylmethyl) malonic acid diethyl ester.

Another object of the invention is a method for producing N and O-protected or N or O-protected, optionally substituted 2-amino-3-(heteroaryl)-carboxylic acid compounds of the general formula I by reacting a diamine of the general formula 1

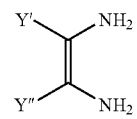

wherein Y' and Y" have the meanings specified above with an α-halogen methylcarbonyl compound of the general formula 2,

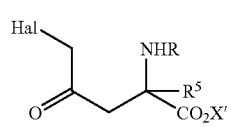

wherein

R, $R^5$, and X' have the meanings specified above and

Hal represents a halogen atom, preferably bromine, in a condensation reaction while adding a trialkyl amine, preferably triethyl amine, in a suitable solvent, preferably ethanol, preferably at a temperature in the range from 5 to 50° C. and by letting the intermediate product, preferably under oxidative conditions, preferably in the presence of oxygen, transform into a compound of the formula I,

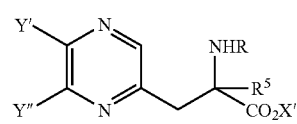

wherein

R, $R^5$, and X' have the meanings specified above, then processing the reaction mixture and isolating the optionally purified target compound.

Preferred α-halogen methylcarbonyl compounds used are 2-amino-2-(3-bromo-2-oxopropyl) malonic acid and 2-amino-5-bromo-4-oxopentanoic acid compounds. These are obtained by reacting an N and/or O-protected 2-amino malonic acid compound with 2,3-dibromopropene into a 2-amino-2-(2-bromoallyl) malonic acid compound and subsequent reaction of this 2-amino-2-(2-bromoallyl) malonic acid compound with N-bromosuccinimide (C.-N. Hsiao et al.: *Synth. Commun.* 20, 1990, pp. 3507-3517). 2,3-Dibromopropene was obtained by bromination of allyl bromide into 1,2,3-tribromopropane (J. R. Johnson et al.: *Org. Synth. Coll. Vol.* 1, 1932, pp. 521-522) and subsequent elimination of hydrogen bromide from 1,2,3-tribromopropane (R. Lespieau et al.: *Org. Synth. Coll. Vol.* 1, 1932, pp. 209-211).

The 2-amino-2-(2-bromoallyl) malonic acid compound obtained using the method of Hisao et al. (loc. cit.) is converted under the conditions named by Leanna and Morton (M. R. Leanna, H. E. Morton: *Tetrahedron Lett.* 34, 1993, pp. 4485-4488) into enantiomerically pure 2-amino-4-bromopent-4-enoic acid compounds [(2-bromoallyl)-glycin derivatives]. The enantiomerically pure 2-amino-4-bromopent-4-enoic acid compounds are obtained from enantiomerically pure 2-amino-5-bromo-4-oxopentanoic acid compounds using the method described by Leanna and Morton (loc. cit.).

The method according to the invention facilitates the production of respective enantiomerically pure β-heteroaryl-α-alanine compounds, also referred to as 2-amino-3-(heteroaryl) propionic acid compounds, using these enantiomerically pure α-halogen methylcarbonyl compounds of the general formula 2.

Another object of the invention is a method for producing N and O-protected or N or O-protected, optionally substituted β-heteroaryl-α-alanine compounds of the general formula I by a) reacting a compound of the formula I

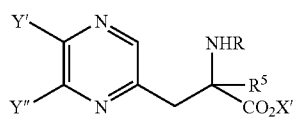

I wherein Y', Y''', X', $R^5$, and R have the meanings specified above, under alkaline conditions, preferably by adding alkali hydroxide, more preferably by adding sodium or potassium hydroxide, in a suitable solvent, preferably in a water-alcohol mixture, preferably under cooling, by means of hydrolysis and subsequent decarboxylation into a compound of the formula I wherein $R^5$ is hydrogen and R and X' have the meanings specified above, then processing the reaction mixture and isolating the compound that may optionally be purified, then hydrolyzing this compound either under acidic conditions preferably set by adding hydrochloric acid, preferably under heating, into a compound of the formula I wherein R and X' each represent hydrogen, then processing the reaction mixture and isolating the compound that may optionally be purified or hydrolyzing the compound of the formula I completely or in part using enzymes or microbacteria into a racemic or partially racemic compound or a mixture of two enantiomorphic compounds of the formula I wherein X' in one compound of the mixture represents hydrogen and in the other compound of the mixture has the meaning specified above, then processing the reaction mixture and isolating the compound(s) that may optionally be purified and hydrolyzing them under acidic conditions preferably set by adding hydrochloric acid, preferably under heating, into a compound of the formula I wherein R and X' each represent hydrogen, then processing the reaction mixture and isolating the compound that may optionally be purified;

b) hydrolyzing a compound of the general formula I wherein Y', Y''', X', $R^5$ and R have the meanings specified above using either enzymes or microbacteria or non-enzymatically or non-microbacterially into a compound of the formula I in which Y', Y''' and R have the meanings specified above and X' as well as X'' represent hydrogen and decarboxylating this compound using enzymes or microbacteria into an enantiomerically pure or partially racematic compound of the formula I wherein Y', Y''' and $R^5$ have the meanings specified above and X' and $R^5$ represent hydrogen;

c) enzymatically decarboxylating and saponifying a compound of formula I wherein Y', Y''', X', $R^5$ and R have the meanings specified above into a compound of formula I wherein R has the meaning specified above and X' is hydrogen, then processing the reaction mixture, isolating the optionally purified compound and hydrolyzing it in an acidic environment, preferably by adding hydrochloric acid, preferably by heating, into a compound of formula I wherein R and X' each represent hydrogen, then processing the reaction mixture and isolating the optionally purified compound;

d) decarboxylating and hydrolyzing a compound of formula I wherein Y', Y''', X', $R^5$ and R have the meanings specified above in an acidic environment, preferably by adding hydrochloric acid, preferably by heating, into a compound of formula I wherein R, $R^5$ and X' each represent hydrogen, then processing the reaction mixture and isolating the optionally purified compound.

Another object of the invention is a method for producing N and O-protected or N or O-protected β-heteroaryl-α-alanines by a) reacting a compound of formula I wherein R, $R^5$ and X' each represent hydrogen with an activated alkyloxycarbonyl compound (see page 6) in the presence of a suitable base and in a suitable solvent to a compound of formula I wherein R represents the alkoxy residue, $R^5$ and X' represent hydrogen, then processing the reaction mixture and isolating the optionally purified compound, or b) reacting a compound of formula I wherein R and $R^5$ are hydrogen and X' is hydrogen, an alkyl or arylalkyl residue with acyl donors into compounds of formula I wherein R is an acyl residue and X' is hydrogen, an alkyl or arylalkyl residue.

Preferred is a method for producing N-fmoc-protected, optionally substituted β-heteroaryl-α-alanine compounds of the general formula I wherein $R^5$ represents hydrogen and R represents the f-moc residue in crystalline form in by reacting a compound of formula I wherein R, $R^5$ and X' each represent hydrogen with N-(fluorene-9-yl-methoxycarbonyloxy)-succinimide or fluorene-9-yl-methoxycarbonyl chloride in a solvent, preferably water, in the presence of a mild inorganic base, preferably sodium or potassium carbonate, and/or in the presence of an organic base, preferably a tertiary organic amine, more preferred in the presence of N-ethyldiisopropyl amine at 0° C. to 50° C., preferably in the range from 10°C. to 30° C.; washing the basic aqueous reaction mixture—optionally multiple times—with a suitable solvent, acidifying the aqueous phase, preferably with hydrochloric acid, extracting the acidic aqueous phase—optionally multiple times—with a suitable chlorinated solvent, preferably dichloromethane, drying the organic phase, and liberating it at least partially or completely from the solvent.

To isolate and purify the N-fmoc-protected, optionally substituted β-heteroaryl-α-alanine compounds, the product is dissolved in a chlorinated solvent, preferably in dichloromethane, and the chlorinated solvent then is gradually displaced from the mixture of solvents by continuously adding another solvent that is less volatile than the first solvent. Ethyl acetate is preferred for use as the second non-chlorinated solvent. In this way, the portion of chlorinated, more volatile solvent lost by evaporation is gradually replaced by a mixture of solvents in which the ratio of chlorinated to non-chlorinated solvent is preferably reduced from 1:1 to 1:10. In this method of isolating the N-fmoc-heteroaryl-α-alanine compound, the product is gradually precipitated from the solution in crystalline form.

After isolating the N-fmoc-heteroaryl-α-alanine compound, the crystalline crude product is once again dissolved under heating in a chlorinated solvent, preferably dichloromethane, optionally together with an alcohol, preferably ethanol, and the resulting solution is intermixed with activated carbon, then the activated carbon is filtered off, the filtrate is liberated from solvent, and the crystallization method described above is repeated for purification. The parent compounds used are commercially available or can be produced using common methods known to an expert skilled in the art.

The reactions are known to an expert skilled in the art from the relevant literature.

The solvents and reaction conditions used in the respective step of the method are common solvents and reaction conditions for these reaction types.

The free bases of the respective compounds according to the invention can be transformed into the respective salts, for example by reacting them with an inorganic or organic acid.

The solvates can be obtained by crystallizing the compounds according to the invention.

Inasmuch as the compounds according to the invention or their precursors are obtained as mixtures of their enantiomers/diastereomers—including their racemates—using the production method of the invention, they can be separated, and optionally isolated, using methods known to an expert skilled in the art. One option is enzymatic racemate splitting during enzymatic saponification of carbonic esters.

Yet another object of the invention is the use of N and O-protected, optionally substituted 2-amino-2-(heteroarylmethyl) carboxylic acid compounds of the general formula I

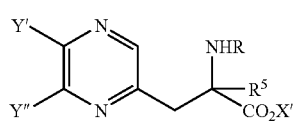

wherein Y', Y''', X', $R^5$, and R have the meanings specified above, for producing N-protected, optionally substituted β-heteroaryl-α-alanine compounds of the general formula I wherein $R^5$ is hydrogen and Y', Y''', X', and R have the meanings specified above.

EXAMPLES

Example 1

Condensation of 2-acetamido-2-(3-bromo-2-oxopropyl) malonic acid diethyl ester with 1,2-phenylendiamine yielding 2-acetamido-2-(2-quinoxalinylmethyl) malonic acid diethyl ester 151 g (1.39 mol) of 1.2-phenylenediamine were suspended under stirring in 4 l of ethanol in a 20 l round flask. A solution of 516 g (1.45 mol) 2-acetamido-2-(3-bromo-2-oxopropyl)-malonic acid diethyl ester in 7 l ethanol was slowly added by dropping over 48 hours. At the same time, a solution of 180 ml (1.3 mol) triethylamine in 1 l ethanol was added by dropping from a separate tap funnel so that the pH value of the reaction solution did not fall below pH 4. The reaction batch was kept agitated for 3 days after completing the addition of α-bromomethyl ketone. The yellowish brown solution was then liberated from the solvent in a vacuum. The residue was immediately taken up under slight heating in 2.5 l ethyl acetate and allowed to cool down. The triethyl ammonium hydrobromide precipitate that developed after some time was sucked off and washed with ethyl acetate. The filtrate was heated with 25 g of activated carbon to about 50° C. and stirred for 15 minutes, then the solution was filtered off using a frit filled with silica gel and washed. The filtrate was reduced by evaporation to about 900 ml in which process a portion of the product precipitated as yellow crystal needles. 250 ml hexane were added to the batch and allowed to stand for some hours at 4° C. The precipitated product was sucked off and recrystallized from an ethyl acetate-hexane mixture. The parent lye was purified by chromatography. The overall yield of 2-acetamido-2-(2-quinoxalinylmethyl)-malonic acid diethyl ester was 70% of the theoretical yield.

Melting point 140 to 141° C.

| $C_{18}H_{21}N_3O_5$ calculated | (359.38) C 60.16 H 5.89 N 11.69 | found | C 60.03 H 5.63 N 11.25 |
|---|---|---|---|

$^1$H-NMR (270 MHz, CDCl$_3$): δ=8.6 (s, 1H), 8.05 (m, 1H), 7.85 (m, 1H), 7.65 (m, 2H), 6.75 (s, 1H), 4.25 (q, 4H), 4.05 (s, 2H), 1.90 (s, 3H), 1.25 (t, 6H). $^{13}$C-NMR (67.9 MHz, CDCl$_3$): δ=169.5, 167.3, 152.0, 146.1, 141.7, 141.4, 130.0, 129.5, 129.2, 128.8, 66.0, 62.8, 37.9, 22.9, 13.9.

Example 2

Monosaponification and decarboxylation of 2-acetamido-2-(2-quinoxalinylmethyl) malonic acid diethyl ester into 2-acetamido-3-(2-quinoxalinyl) propionic acid ethyl ester 10 g (27.8 mmol) 2-acetamido-2-(2-quinoxalinylmethyl) malonic acid diethyl ester were suspended in a mixture of 75 ml ethanol and 10 ml water and cooled to 5° C. in an ice bath. 2.2 g potassium hydroxide were dissolved in 8 ml water and added to the cooled suspension. After removing the ice bath, the batch was heated to room temperature within 45 minutes and stirred for 30 minutes at room temperature. After another 15 minutes of stirring at room temperature, the solution was cooled in an ice bath again and its pH value set to pH 5 by adding drops of concentrated hydrochloric acid. The solution was then completely liberated from solvent in a vacuum, taken up twice in about 50 ml ethanol, the solvent being separated off in a vacuum each time. The residue was taken up under heating in 250 ml of an ethyl acetate-dichloromethane mixture at a ratio of 1:1 and the undissolved salts were filtered off. The filtrate was liberated from the solvent once again, the residue taken up in 100 ml 1,4-dioxane and heated to 100° C. in about 4 hours. The solvent was removed in a vacuum, and the residue dissolved in 150 ml ethyl acetate. The solution was filtered after cooling. The filtrate was concentrated in a vacuum to about 100 ml mixed with little hexane, and kept at 4° C. for 12 hours. The precipitated crystals were sucked off. The product yield was 7.2 g (88% of the theoretical yield).

Melting point 121 to 123° C.

| $C_{15}H_{17}N_3O_3$ calculated | (287.32) C 62.71 H 5.69 N 14.62 | found | C 62.54 H 5.58 N 14.30 |
|---|---|---|---|

$^1$H-NMR (400 MHz, CDCl$_3$): δ=8.70 (s, 1H), 8.08 (m, 1H), 7.94 (m, 1H), 7.75 (m, 2H), 6.85 (d, 1H), 5.10 (dt, 1H), 4.18 (q, 2H), 3.58 (dd, 2H), 1.98 (s, 3H), 1.28 (t, 3H). $^{13}$C-

NMR (100 MHz, CDCl$_3$): δ=171.1, 169.8, 152.7, 145.8, 141.7, 141.4, 130.3, 129.6, 129.3, 128.9, 62.0, 51.5, 37.5, 23.7, 14.6.

Example 3

Decarboxylation and acidic hydrolysis of 2-acetamido-2-(2-quinoxal inylmethyl) malonic acid diethyl ester into β-(2-quinoxalinyl)-α-alanine hydrochlor 100 g (278 mmol) 2-acetamido-2-(2-quinoxalinylmethyl) malonic acid d iethylester were showered with 600 ml of 20% hydrochloric acid. A dark violet solution developed. It was heated to about 108° C. over 12 hours. Then the hydrochloric acid was distilled off in a vacuum, the residue was taken up twice in 300 ml water and the solvent was subsequently removed in a vacuum. The residue was absorbed in 500 l water, the solution was mixed with 5 g activated carbon and stirred for 15 minutes at 65° C. The activated carbon was filtered off as long as the solution was still hot, and the filter residue was washed with about 150 ml of water heated to 50° C. The resulting aqueous solution of amino acid hydrochloride was used as is.

Example 4

Decarboxylation and hydrolysis of 2-acetamido-2-(2-quinoxalinylmethyl) malonic acid diethyl ester into β-(2-quinoxalinyl)-α-alanine 92 g (256 mmol) 2-acetamido-2-(2-quinoxalinyimethyl) malonic acid diethyl ester were showered with 480 ml of 19% hydrochloric acid. A dark violet solution developed. It was heated to about 98° C. over 10 hours. Then the hydrochloric acid was distilled off the now dark green solution in a vacuum, the residue was taken up twice in 300 ml water and the solvent was subsequently removed in a vacuum. The residue was taken up in 400 ml water, the solution was mixed with 5 g activated carbon and stirred for 15 minutes at 60° C. The activated carbon was filtered off as long as the solution was still hot, and the filter residue was washed with about 120 ml of water heated to 45° C. The solution was concentrated in a vacuum to 400 ml. The solution was cooled in an ice bath to about 5° C. and neutralized under stirring by adding drops of ammonia water. The free amino acid started to precipitate with rising pH value. The batch was set to a pH value of 7, and the precipitate that formed was sucked off using a filtering frit. The filter residue was first washed with water, then with ethanol. The amino acid yield was 44 g (79% of the theoretical yield).

Example 5

Preparation of N-boc-β-(2-quinoxalinyl)-α-alanine

The hydrochloric acid solution of β-(2-quinoxalinyl)-α-alanine obtained in Example 3 was cooled down to 5° C. in an ice bath and set to a pH value of 12 using 40% caustic soda solution. A spatula tipful of 4-dimethylaminopyridine was added and the solution kept at 15° C. 90 g tert.-butyloxycarbonyl anhydride (boc anhydride) were added by dropping within 30 minutes. The batch was agitated for 3 hours. Then some more caustic soda solution and 25 g butyloxycarbonyl anhydride were added. The batch was stirred for 5 hours, and a pH value of 5 was cautiously set using hydrochloric acid at room temperature. The solution was evaporated to dryness in a vacuum, then the residue was taken up in ethanol several times and the solvent was removed in a vacuum. The residue was dried in a vacuum and suspended in a mixture of ethanol and ethyl acetate at a ratio of 8 to 3. The suspension was heated to dissolve the organic ingredients. The solution was filtered after cooling. 4 g of activated carbon were added to the clear filtrate, the batch was stirred for 15 minutes at 40° C., and the activated carbon was filtered off. The filtrate was kept at 4° C. and slowly mixed with some hexane. Crystals of the product separated out after some time. These were filtered off and washed in a mixture of ethyl acetate and methanol at a ratio of 10 to 1. The crystals were dried in a vacuum. The product yield was 59 g (67% of the theoretical yield).

Melting point: 221 to 224° C. (decomposition). $^1$H-NMR (400 MHz, DMSO-d$_6$): δ=8.80 (s, 1H), 8.00 (m, 2H), 7.75 (m, 2H), 6.15 (d, 1H), 4.10 (m, 1H), 3.45 (m, 1H), 3.10 (m, 1H), 1.20 (s, 9H). $^{13}$C-NMR (100 MHz, DMSO-d$_6$): δ=174.3, 156.6, 155.1, 147.6, 142.1, 141.1, 130.1, 129.4, 129.3, 129.2, 78.1, 41.1, 56.5, 28.9.

Example 6

Preparation of N-fmoc-β-(2-quinoxalinyl)-α-alanine 44 g (±)-β-(2-quinoxalinyl)-α-alanine from Example 4 were suspended in 500 ml water and cooled in an ice bath to 10° C. 45 g sodium carbonate were added to the suspension. The batch was stirred at 10° C. until the suspension had turned into a homogeneous solution. 150 ml 1,4-dioxane and, after 30 minutes, 10 ml N-ethyl diisopropylamine were added to the reddish brown solution. Within 2 hours, about 75 g fluorene-9-yl-methoxycarbonyl chloride (FmocCl), dissolved in 1,4-dioxane were added by dropping until the TLC monitoring system showed no more free amino acid. The pH value of the reaction solution is kept alkaline by adding more sodium carbonate. The alkaline solution was then washed five times with ethyl acetate/hexane mixtures at ratios from 3:1 to 2:1 to remove most by-products. The aqueous phase was then set to a pH value of 4 using concentrated hydrochloric acid. The aqueous phase was extracted four times, each time with 250 ml dichloromethane, and the combined dichloromethane phases were dried over magnesium sulfate. The drying agent was filtered off and washed with dichloromethane. The filtrate was concentrated in a vacuum to a volume of 200 ml and mixed with 3 ml acetic acid. The solution was allowed to stand uncovered under an exhaust hood to allow the solvent to gradually evaporate. A brown paste-like mass had formed after some days. Very small portions of a mixture of dichloromethane and ethyl acetate with a constantly declining dichloromethane content were added within 4 days to the thick paste, the dichloromethane to ethyl acetate ratio being reduced from 1:1 to 1:10. Only as much ethyl acetate was added as was required to dissolve an initial turbidity but the batch kept pasty and no clear solution was formed. After some days, voluminous golden crystals had formed. After most of the product had turned into a golden crystal mass, it was sucked off and washed with some ethyl acetate and a mixture of ethyl acetate and hexane. The filter residue weighed about 65 g after drying in a vacuum. The crude product had a melting range from 115 to 135° C.

The crude product was dissolved once again in dichloromethane under heating and adding ethanol. The solution was mixed with 5 g activated carbon and stirred for 10 minutes, then the activated carbon was filtered off.

The filtrate was completely liberated from the solvent, the pasty residue dissolved in as little dichloromethane as possible, and mixed with 1 ml acetic acid. The solution was once again allowed to stand uncovered under an exhaust hood, and dichloromethane was gradually replaced with ethyl acetate as described above. A yellowy-gold precipitate of the product formed after 24 hours. The yellowy-gold precipitate increased when adding small portions of dichloromethane and a mixture of ethyl acetate and hexane at a 1:1 ratio; the solvent added was dosed to dissolving an initial turbidity and not to let the dichloromethane evaporate completely. The major quantity of the product had precipitated as a golden sediment after 3 to 4 days. The precipitate was sucked off and washed with a mixture of ethyl acetate and hexane at a 1:1 ratio. 47 g (53% of the theoretical yield) of product with 91% purity were obtained. Using the method described above, the material obtained was purified to about 94% purity.

Melting point 180 to 183° C., decomposition. $^1$H-NMR (400 MHz, DMSO-$d_6$): δ=8.90 (s, 1H), 8.20-7.75 (m, 6H), 7.60-7.40 (m, 2H), 7.35-7.0 (m, 4H), 4.75 (m, 1H), 4.20 (mc, 2H), 3.60-3.20 (m, 3H). $^{13}$C-NMR (100 MHz, DMSO-$d_6$): δ=172.9, 155.6, 154.0, 146.6 143.6, 141.4, 140.8, 140.6, 130.1, 129.4, 128.8, 128.6, 127.5, 126.9, 125.0, 119.9, 65.6, 53.5, 46.5, 36.9.

The invention claimed is:

1. β-heteroaryl-α-alanine compounds of the structural formula I,

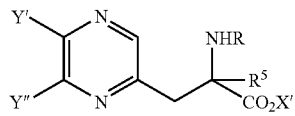

wherein
Y' and Y" together form a

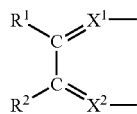

chain wherein
$X^1$ is nitrogen or a $CR^3$ group,
$X^2$ is nitrogen or a $CR^4$ group,
$R^1$, $R^2$, $R^3$, and $R^4$ are the same or different and each independently is selected from the group consisting of hydrogen, halogen, a $C_{1-3}$ alkyl residue, a $C_{1-3}$ alkoxy residue, a $CF_3$ residue, a $CHF_2$ residue, and a $CH_2F$ residue,
R is an alkoxycarbonyl residue selected from the group consisting of tert-butoxycarbonyl, 9-fluorenylmethoxycarbonyl, methyloxycarbonyl, ethyloxycarbonyl, allyloxycarbonyl, benzyloxycarbonyl, 9-(2,7-dibromo)-fluorenylmethyloxycarbonyl, 9-[2,7-bis(trimethylsilyl) 9-fluorenylmethyloxycarbonyl, 9-(2,6-di-tert-butyl)-fluorenylmethyloxycarbonyl, 9-(2,7-di-tert-butyl)-fluorenylmethyloxycarbonyl, 2,2,2-trichloroethyloxycarbonyl, 2-trimethylsilylethyloxycarbonyl, p-methoxybenzyloxycarbonyl, p-nitrobenzyloxycarbonyl, 4-methysulfinylbenzyloxycarbonyl, and 6-nitroveratryloxycarbonyl residues
or an acyl residue selected from the group consisting of acetyl, trifluoroacetyl, propionyl, pivaloyl, 4-pentenoyl, 2,2-dimethyl-4-pentenoyl, benzoyl, and phthalyl residues,
$R^5$ is a hydrogen atom or a $CO_2X''$ group in which X" represents an alkyl, aryl, or amino group —$NR^6R^7$ in which $R^6$ and $R^7$ are the same or different and each independently represents a hydrogen, an alkyl or aryl residue and,
X' is an alkyl group selected from the group consisting of methyl, ethyl, propyl, butyl, benzyl, aryl-substituted benzyl, trimethysilyethyl, tert-butyl-neopentyl 2,2,2,-trichloroethyl residues,
or diastereomers, enantiomers or mixtures thereof, or free bases, salts, or solutions thereof.

2. The compounds according to claim 1, wherein
R is an acetyl group and
X' is an ethyl group, and
$R^1$, $R^2$, $R^3$, and $R^4$ are same or different and may each represent a hydrogen, fluorine, chlorine, bromine atom, a methyl residue, an ethyl residue, a methoxy residue, an ethoxy residue, and/or a $CF_3$ residue.

3. The compounds according to claim 1, wherein
X' and X" are same or different and each represent a $C_{1-3}$ alkyl residue,
R represents an alkyloxycarbonyl residue selected from the group containing tert-butoxycarbonyl, 9-fluorenylinethoxycarbonyl, methyloxycarbonyl, ethyloxycarbonyl, allyloxycarbonyl, benzyloxycarbonyl, 9-(2,7-dibromo)-fluorenylmethyloxycarbonyl, 9-(2,7-di-tert-butyl)-fluorenylmethyloxycarbonyl trichloroethyloxycarbonyl, 2-trimethylsilylethyloxycarbonyl, p-methoxybenzyloxycarbonyl, p-nitrobenzyloxycarbonyl, 4-methylsulfmylbenzyloxycarbonyl, and 6-nitroveratryloxycarbonyl residues or an acyl residue selected from the group containing acetyl, trifluoroacetyl, propionyl, pivaloyl, 4-pentenoyl, 2,2-dimethyl-4-pentenoyl, benzoyl, phthalyl residues, and
$R^1$, $R^2$, $R^3$, and $R^4$ are same or different and each represent a hydrogen, halogen atom, a $C_{1-3}$ alkyl residue, a $C_{1-3}$ alkoxy residue, a $CF_3$ residue, a $CHF_2$ residue, or a $CH_2F$ residue.

4. The compounds according to claim 1, wherein the β-heteroaryl-α-alanine compounds are selected from the group consisting of
2-acetamido-2-(2-quinoxalinylmethyl) malonic acid diethyl ester, 2-benzamido-2-(2-quinoxalinylmethyl) malonic acid diethyl ester, 2-phthalylimino-2-(2-quinoxalinylmethyl) malonic acid diethyl ester, 2-benzamido-2-(2-quinoxalinylmethyl) malonic acid diethyl ester, 2-phthalylimino-2-(2-quinoxalinylmethyl) malonic acid diethyl ester, and 2-acetamido-2-(2-quinoxalinylmethyl) malonic acid diethyl ester, has been replaced with 2-acetamido-2-(2-quinoxalinylmethyl) malonic acid diethyl ester, 2-benzamido-2-(2-quinoxalinylmethyl) malonic acid diethyl ester, and 2-phthalylimino-2-(2-quinoxalinylmethyl) malonic acid diethyl ester.

5. β-heteroaryl-α-alanine compounds of the structural formula 1 according to claim 1,

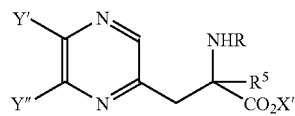

wherein
$R^5$ is a hydrogen atom and
Y' and Y", X' and R have the meanings specified in claim 1.

6. The compounds according to claim 1, wherein R is an alkoxycarbonyl residue selected from the group consisting of tert-butoxycarbonyl, 9-fluorenylmethoxycarbonyl, methyloxycarbonyl, ethyloxycarbonyl, allyloxycarbonyl, benzyloxycarbonyl, 9-(2,7-dibromo)-fluorenylmethyloxycarbonyl, 9-[2,7-bis(trimethylsilyl)]-fluorenylmethyloxycarbonyl, 9-(2,6-di-tert-butyl)-fluorenylmethyloxycarbonyl, 9-(2,7-di-tert-butyl)-fluorenylmethyloxycarbonyl, 2,2,2-trichloroethyloxycarbonyl, 2-trimethylsilylethyloxycarbonyl, p-methoxybenzyloxycarbonyl, p-nitrobenzyloxycarbonyl, 4-methysulfinylbenzyloxycarbonyl, and 6-nitroveratryloxycarbonyl residues.

* * * * *

UNITED STATES PATENT AND TRADEMARK OFFICE
CERTIFICATE OF CORRECTION

PATENT NO.        : 7,626,022 B2                          Page 1 of 1
APPLICATION NO. : 10/889355
DATED             : December 1, 2009
INVENTOR(S)       : Stefan Oehlinger It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 895 days.

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,626,022 B2 | |
| APPLICATION NO. | : 10/889355 | |
| DATED | : December 1, 2009 | |
| INVENTOR(S) | : Oehlinger | |

It is certified that error appears in the above-identified patent and that said Letters Patent is hereby corrected as shown below:

Column 11, Line 55, Claim 1, "(trimethylsilyl) 9-" should read -- (trimethylsilyl)]- --.

Column 12, Lines 23-24, Claim 3, "9-fluorenylinethoxycarbonyl," should read
-- 9-fluorenylmethoxycarbonyl, --;

Claim 3, Lines 26-27, "9-(2,7-di-tert-butyl)- fluorenylmethyloxycarbonyl,"
should read -- 9-[2,7-bis(trimethylsilyl)]-fluorenylmethyloxycarbonyl, --;

Claim 3, Lines 27-28, delete "trichloroethyloxycarbonyl," and insert the following:
-- 9-(2,6-di-tert-butyl)-fluorenylmethyloxycarbonyl, 9-(2,7-di-tert-butyl)-
fluorenylmethyloxycarbonyl, 2,2,2-trichloroethyloxycarbonyl, --;

Claim 3, Line 30, "4-methylsulfmylbenzyloxycarbonyl," should read
-- 4-methylsulfinylbenzyloxycarbonyl, --.

Column 12, Line 39-53, Claim 4 should read
-- 4. The compounds according to claim 1, wherein the β-heteroaryl-α-alanine compounds
are selected from the group consisting of
2-acetamido-3-(2-quinoxalinyl) propionic acid ethyl ester,
N-boc-β-(2-quinoxalinyl)-α-alanine,
N-fmoc-β-(2-quinoxalinyl )-α-alanine,
N-acetyl-β-(2-quinoxalinyl)-α-alanine,
N-phthalimido-β-(2-quinoxalinyl)-α-alanine,
N-(pent-4-enoyl)-β-(2-quinoxalinyl)-α-alanine,
2-acetamido-2-(2-quinoxalinylmethyl) malonic acid diethyl ester,
2-benzamido-2-(2-quinoxalinylmethyl) malonic acid diethyl ester, and
2-phthalylimino-2-(2-quinoxalinylmethyl) malonic acid diethyl ester. --.

Signed and Sealed this
First Day of May, 2012

David J. Kappos
*Director of the United States Patent and Trademark Office*